(12) United States Patent
Isola et al.

(10) Patent No.: US 10,182,837 B2
(45) Date of Patent: Jan. 22, 2019

(54) SHEATH COUPLING MEMBER AND ASSOCIATED INSTRUMENT ASSEMBLY

(71) Applicant: Misonix Incorporated, Farmingdale, NY (US)

(72) Inventors: Scott Isola, Deer Park, NY (US); Alexander Darian, Brightwaters, NY (US); Ronald Manna, Valley Stream, NY (US); Dan Voic, Cedar Grove, NJ (US)

(73) Assignee: MISONIX, INC., Farmingdale, NY (US)

( * ) Notice: Subject to any disclaimer, the term of this patent is extended or adjusted under 35 U.S.C. 154(b) by 0 days.

(21) Appl. No.: 13/931,045

(22) Filed: Jun. 28, 2013

(65) Prior Publication Data

US 2015/0005796 A1 Jan. 1, 2015

(51) Int. Cl.
| | | |
|---|---|---|
| *A61B 17/32* | (2006.01) | |
| *A61N 7/02* | (2006.01) | |
| *A61B 17/00* | (2006.01) | |
| *A61B 18/00* | (2006.01) | |

(52) U.S. Cl.
CPC ........ *A61B 17/320068* (2013.01); *A61N 7/02* (2013.01); *A61B 2017/00477* (2013.01); *A61B 2017/00738* (2013.01); *A61B 2017/320084* (2013.01); *A61B 2018/00005* (2013.01); *A61B 2018/00172* (2013.01); *A61B 2018/00601* (2013.01); *A61B 2217/005* (2013.01); *A61B 2218/007* (2013.01)

(58) Field of Classification Search
CPC ..................... A61B 17/320068; A61B 1/0055
USPC .................................................. 606/169, 1
See application file for complete search history.

(56) References Cited

U.S. PATENT DOCUMENTS

| | | | |
|---|---|---|---|
| 3,388,705 A | | 6/1968 | Grosshandler |
| 4,098,298 A | * | 7/1978 | Vohrer .................. F16L 11/112 138/122 |
| 4,690,175 A | | 9/1987 | Ouchi et al. |
| 5,109,889 A | * | 5/1992 | Kanao ..................... F16L 11/15 138/122 |
| 5,287,858 A | * | 2/1994 | Hammerslag .. A61B 17/320758 600/585 |
| 5,454,795 A | * | 10/1995 | Samson ................ A61L 29/041 600/435 |
| 5,695,491 A | * | 12/1997 | Silverstein ....................... 606/1 |
| 5,807,354 A | * | 9/1998 | Kenda ............... A61M 25/0054 604/174 |
| 5,870,354 A | * | 2/1999 | Maruyama ........... G11B 15/026 368/63 |
| 5,871,475 A | * | 2/1999 | Frassica ............ A61M 25/0021 411/411 |
| 5,968,012 A | * | 10/1999 | Ren et al. .................. 604/96.01 |

(Continued)

*Primary Examiner* — Richard Louis
(74) *Attorney, Agent, or Firm* — R. Neil Sudol; Henry D. Coleman

(57) ABSTRACT

A coupling member for an ultrasonic instrument assembly has a tubular body with a first port at a first end and a second port at a second end opposite the first end. A lumen in the body member extends from the first end to the second end so that the first and the second port communicate with one another. The body member is made of a flexible resilient material such as silicone rubber and at least one reinforcement element is joined to the body member. The reinforcement element is configured so as to at least inhibit a collapse of the body member.

14 Claims, 3 Drawing Sheets

(56) References Cited

U.S. PATENT DOCUMENTS

| | | | | |
|---|---|---|---|---|
| 6,019,779 | A * | 2/2000 | Thorud | A61F 2/88 606/198 |
| 6,169,276 | B1 * | 1/2001 | Meyer | 219/553 |
| 6,315,715 | B1 * | 11/2001 | Taylor | A61B 1/018 138/122 |
| 7,279,208 | B1 * | 10/2007 | Goffena | A61L 27/16 428/36.91 |
| 2003/0098084 | A1 * | 5/2003 | Ragner | A47L 9/24 138/129 |
| 2004/0006269 | A1 * | 1/2004 | Novak et al. | 600/437 |
| 2004/0249462 | A1 * | 12/2004 | Huang | 623/17.13 |
| 2005/0000758 | A1 * | 1/2005 | Tarasinski et al. | 188/71.1 |
| 2006/0264906 | A1 * | 11/2006 | Pal | A61M 25/0009 604/523 |
| 2007/0173871 | A1 * | 7/2007 | Houser | A61B 17/320092 606/169 |
| 2008/0021384 | A1 * | 1/2008 | Simpson et al. | 604/102.03 |
| 2008/0125626 | A1 * | 5/2008 | Chang et al. | 600/104 |
| 2013/0053830 | A1 * | 2/2013 | Edwards et al. | 606/1 |

* cited by examiner

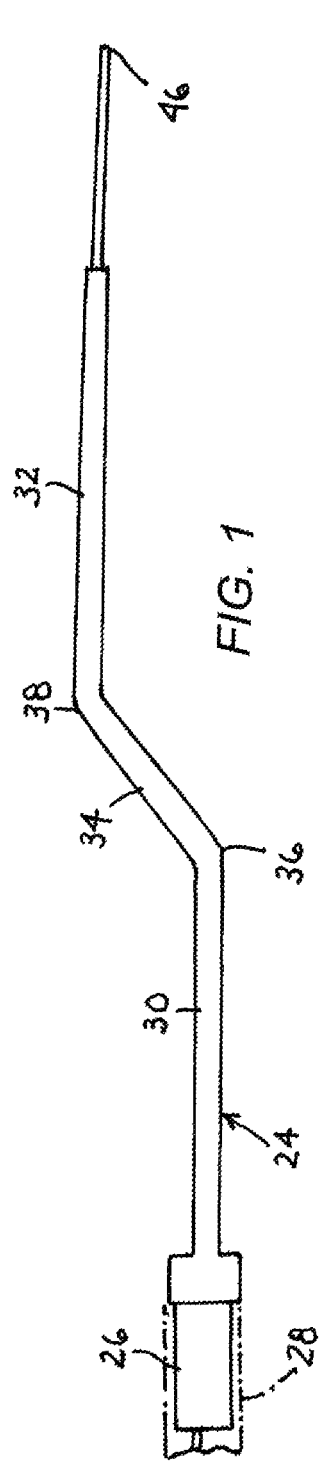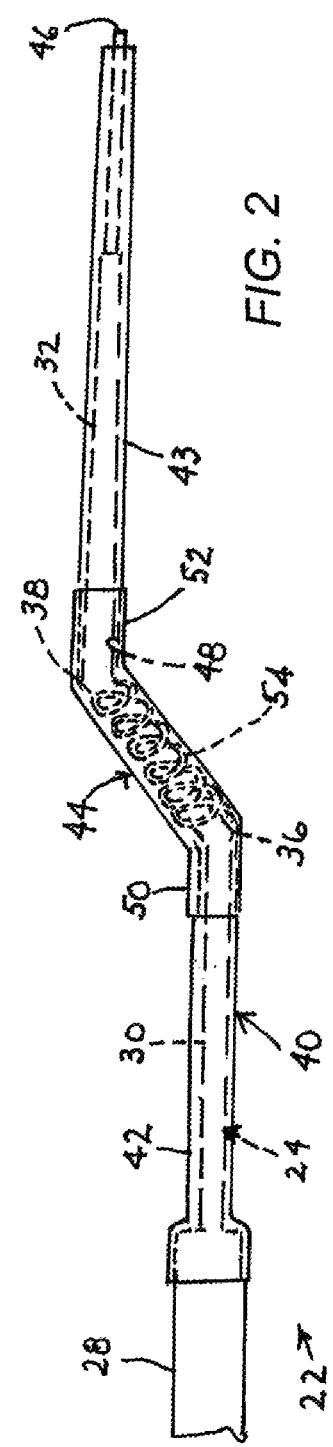

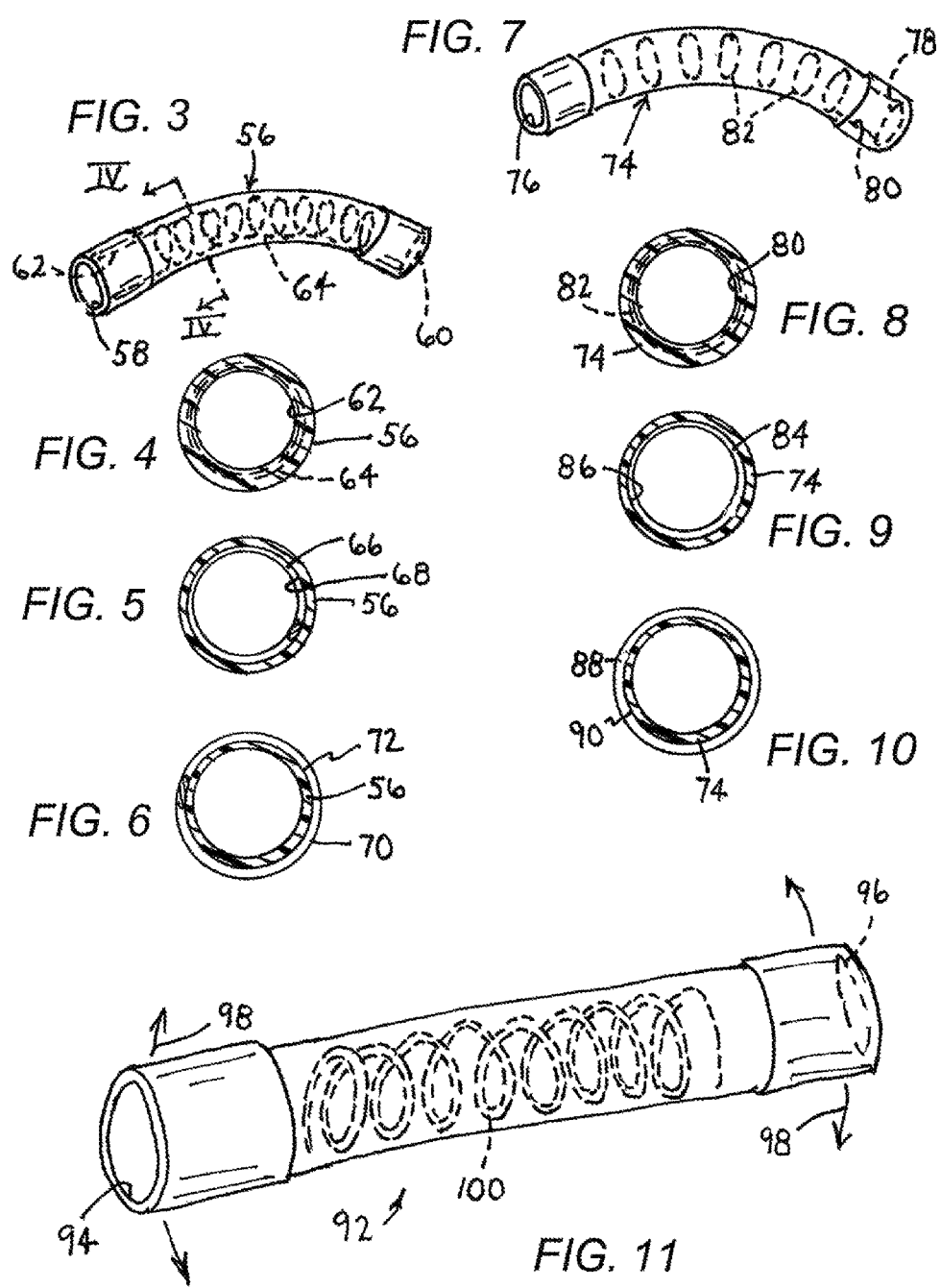

SHEATH COUPLING MEMBER AND ASSOCIATED INSTRUMENT ASSEMBLY

BACKGROUND OF THE INVENTION

This invention pertains to surgical instruments, particularly to ultrasonic instrument assemblies and more particularly to such instrument assemblies with a sheath.

Ultrasonic surgical instruments including incising instruments such as bone cutters and tissue cleaners of debriders are usually provided with sheaths that surround respective vibration-bearing shafts and define therewith channels for the passage of cooling liquid and/or suction for debris removal. Typically, such ultrasonic surgical instruments have probes or shafts that formed with a bend for rendering the instruments more ergonomic, that is, facilitative of accessing various surgical sites. The sheaths are generally rigid in part for maintaining the integrity of the flow channels but also for preventing or minimizing contact between the sheaths and the vibrating shafts, which may have an untoward effect on the sheaths. However, where an instrument shaft has a bend, it is in the interests of manufacturing expediency to provide a flexible connector at the bend. Such a connector joins two rigid sections of sheath, a proximal section and a distal section.

SUMMARY OF THE INVENTION

A problem has been observed with the use of flexible connectors over the bends in ultrasonic instrument shafts. The flexible connector can be temporarily collapsed into contact with the vibrating instrument shaft, for instance, upon inadvertent contact with another object such as part of a patient or a surgeon's hand or arm. The contact can transmit ultrasonic vibration through the material of the connector, resulting in potential undesirable burning of the patient or the surgeon. The present invention seeks to eliminate or at least reduce this problem.

A coupling member for an ultrasonic instrument assembly comprises, in accordance with the present invention, a tubular body member having a first port at a first end and a second port at a second end opposite the first end, the body member further having a lumen or channel extending from the first end to the second end so that the first and the second port communicate with one another. The body member is made of a flexible resilient material such as silicone rubber and at least one reinforcement element is joined to the body member. The reinforcement element is configured so as to at least inhibit a collapse of the body member.

The reinforcement element preferably extends at least partially circumferentially about the body member. The reinforcement element may take the form of a helical or spiral insert. Alternatively, in another embodiment, the reinforcement member takes the form of a ring, e.g., a slotted ring. In the latter case, the reinforcement element is preferably one of a plurality of substantially identical reinforcement rings spaced from each other longitudinally along the tubular body member.

Pursuant to alternative additional features of the present invention, the one or more reinforcement elements are either embedded in the flexible resilient material of the body member or attached to an inner surface of the body member.

Typically, the reinforcement element is made of a more rigid material than the flexible resilient material of the body member. Where the reinforcement element is disposed on the inner surface of the body member, the reinforcement member is best made of a non-metallic material, such as a thermoplastic polymeric material. Where the reinforcement element is embedded in the body member, the reinforcement element may be made of a metal or alloy or a non-metallic material, such as a thermoplastic polymeric material.

A sheath for an ultrasonic instrument assembly comprises, in accordance with the present invention, a substantially rigid first sheath section, a substantially rigid second sheath section, a tubular body member, and at least one reinforcement element. The body member is connected at one end to the first sheath section and at an opposite end to the second sheath section so that the first sheath section and the second sheath section communicate with one another. The body member is made of a flexible resilient material such as silicone rubber. The reinforcement element is joined to the body member and configured so as to at least inhibit a collapse of the body member.

The reinforcement element may extend at least partially circumferentially about the body member. The reinforcement element may take the form of a helical or spiral insert and made be embedded in the body member or attached thereto along an inner surface thereof.

The reinforcement element may be one of a plurality of reinforcement elements joined to the body member and collectively configured for at least inhibiting a collapse of the body member. Preferably, but not necessarily, the reinforcement elements are substantially identical and spaced longitudinally or axially along the body member. The reinforcement elements may be rings, integral or slotted.

Preferably, the reinforcement element is made of a more rigid material than the flexible resilient material of the body member An ultrasonic instrument assembly comprises, in accordance with the present invention, a handpiece, a probe or instrument shaft extending from one end of the handpiece, a proximal sheath portion connected to the handpiece and surrounding a proximal end portion of the probe or instrument shaft, a distal sheath portion surrounding a distal end portion of the probe or instrument shaft, and a tubular coupling member. The coupling member has a lumen or channel, a proximal end section disposed in substantially fluid tight contact with the proximal sheath portion, and a distal end section disposed in substantially fluid tight contact with the distal sheath portion. The body member is made of a flexible resilient material and is provided with at least one reinforcement element joined to the body member. The reinforcement element is configured so as to at least inhibit a collapse of the body member.

The reinforcement element may be a ring or helical or spiral insert. The reinforcement element is made of a more rigid material than the flexible resilient material of the body member. The reinforcement element may be embedded in the flexible resilient material of the body member or attached to an inner surface of the body member.

Pursuant to another feature of the present invention, the tubular body member is provided with at least one expansion portion. The expansion portion may include an outwardly deformed portion of the tubular body member, such as a spiral bellows bubble or rib.

In an ultrasonic tool assembly provided with a sheath coupling member as described herein, incidences of unintended burning of human tissue are reduced, owing to the reduction if not elimination of instances of sheath collapse particularly at bends in the shaft or probe of the ultrasonic tool assembly.

BRIEF DESCRIPTION OF THE DRAWING

FIG. 1 is a side elevational view of an ultrasonic instrument including a bent probe shaft and a handpiece with a transducer array for generating ultrasonic vibrations in the probe shaft.

FIG. 2 is a side elevational view of an ultrasonic instrument assembly in accordance with the present invention, which includes the instrument of FIG. 1 and a sheath in accordance with the present invention, the sheath in turn including a coupling member or sheath connector in accordance with the present invention.

FIG. 3 is schematic perspective view of a coupling member or sheath connector similar to that of FIG. 2.

FIG. 4 is a transverse cross-sectional view taken along line IV-IV in FIG. 3.

FIG. 5 is a transverse cross-sectional view similar to FIG. 4, showing a modification to the coupling member or sheath connector of FIGS. 3 and 4.

FIG. 6 is a transverse cross-sectional view similar to FIGS. 4 and 5, showing another modification to the coupling member or sheath connector of FIGS. 3 and 4.

FIG. 7 is schematic perspective view of another coupling member or sheath connector in accordance with the present invention.

FIG. 8 is a transverse cross-sectional view taken along line VIII-VIII in FIG. 7.

FIG. 9 is a transverse cross-sectional view similar to FIG. 8, showing a modification to the coupling member or sheath connector of FIGS. 7 and 8.

FIG. 10 is a transverse cross-sectional view similar to FIGS. 8 and 9, showing another modification to the coupling member or sheath connector of FIGS. 7 and 8.

FIG. 11 is a schematic perspective view of a further coupling member or sheath connector in accordance with the present invention.

DETAILED DESCRIPTION

Figure 12:
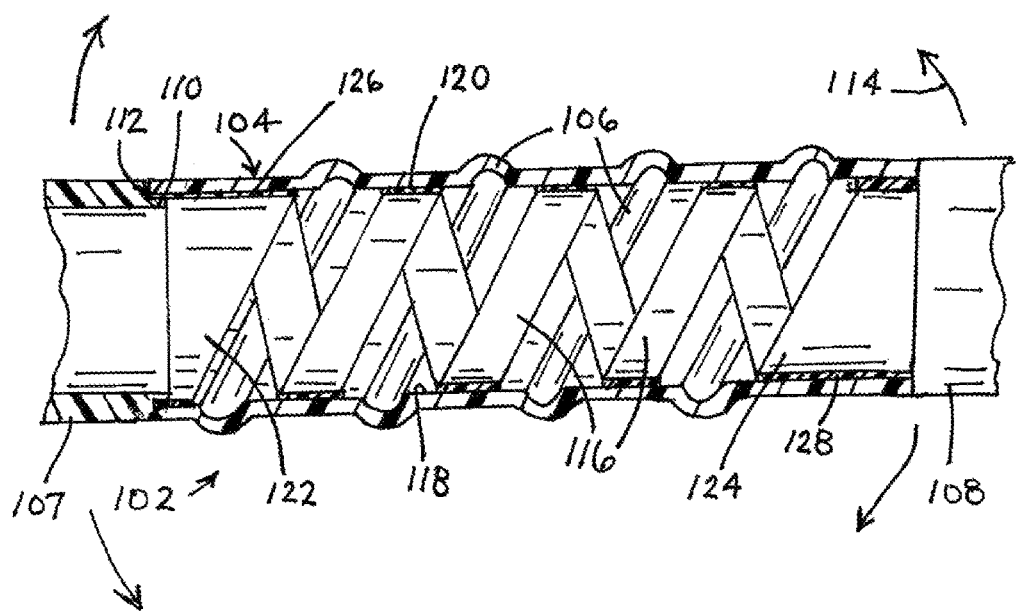
FIG. 12 is a longitudinal cross-sectional view, on a larger scale, of yet another coupling member or sheath connector in accordance with the present invention.

As illustrated in FIGS. 1 and 2, an ultrasonic instrument assembly 22 comprises a probe or instrument shaft 24 connected at a proximal end to a piezoelectric or magnetoconstrictive transducer array 26 in a handpiece 28. Probe or instrument shaft 24 extends from one end of handpiece 28 and includes (i) a linear proximal section 30, (ii) a linear distal section 32, and (iii) a linear intermediate section 34 extending between a distal end of proximal probe section 30 and a proximal end of distal probe section 32. Intermediate section 34 is connected to proximal probe section 30 at a joint or bend 36 and to distal probe section 32 at a joint or bend 38.

Ultrasonic instrument assembly 22 further comprises a sheath subassembly 40 including (i) a proximal sheath portion 42 connected to handpiece 28 and surrounding proximal end portion 30 of probe or instrument shaft 24, (ii) a distal sheath portion 43 surrounding distal end portion 32 of probe or instrument shaft 24, and (iii) a tubular coupling member 44. Distal end portion 32 of sheath subassembly 40 terminates proximally of a distal tip 46 of instrument shaft 24, enabling the tip or operative end effector to contact target tissues at a preselected surgical site.

Coupling member 44 is a tubular body having a lumen or channel 48, a proximal end section 50 disposed in substantially fluid tight contact with proximal sheath portion 42, and a distal end section 52 disposed in substantially fluid tight contact with distal sheath portion 43. Coupling body member 44 is made of a flexible resilient material such as silicone rubber and is provided with at least one reinforcement element 54 joined to the body member. Reinforcement element 54 is configured so as to at least inhibit a collapse of the body member 44.

Coupling member 44 has Z-shaped configuration matching the Z-shaped center region of instrument shaft 24. Reinforcement element 54 is in the form of a helical or spiral insert preferably made of a relatively rigid material, such as a thermoplastic polymer or a metal or alloy, which is more rigid than the flexible resilient material of body member 44. Reinforcement element 54 is embedded in and surrounded by the flexible resilient material of body member 44. In an alternative design discussed hereinafter with respect to FIGS. 4 and 9, the reinforcement element(s) may be provided along an inner surface of body member 44, i.e., a surface defining lumen or channel 48. In another alternative design, discussed hereinafter with respect to FIGS. 5 and 10, the reinforcement element(s) may be provided along an outer surface of coupling body member 44.

Reinforcement element 54 may be made from a flat strip of material that is shaped to assume a helical or coiled configuration.

FIGS. 3 and 4 depict a sheath coupling or connector 56 in the form of an arcuate tubular body member having a first port 58 at a first end and a second port 60 at a second end opposite the first end. A lumen 62 in the body member 56 extends from the port 58 at the first end of the tubular body to the port 60 at the second end so that the first and the second port 58 and 60 communicate with one another. Tubular body member 56 is made of a flexible resilient material such as silicone rubber and incorporates at least one helical reinforcement element 64 joined to the body member. Reinforcement element 64 is designed so as to at least inhibit a collapse of sheath coupling body member 56.

Reinforcement element 64 extends circumferentially in multiple turns about the sheath coupling member 56. As depicted in FIG. 4, reinforcement helix 64 is embedded in and surrounded by sheath coupling member 56. Alternatively or additionally, sheath coupling member 56 may have a helical reinforcement element 66 that is adhered to an inner surface 68 of the coupling member, as illustrated in FIG. 5, and/or a helical reinforcement element 70 that is attached along an outer surface 72 of the coupling member 56, as illustrated in FIG. 6.

FIGS. 7 and 8 show a sheath connector or coupling member 74 in the form of a tubular body member preformed to have an arcuate configuration with a first port 76 at a first end and a second port 78 at a second end opposite the first end. A lumen 80 in the body member 74 extends from the port 76 at the first end of the tubular body to the port 78 at the second end so that the first and the second port 76 and 78 communicate with one another. Tubular body member 74 is made of a flexible resilient material such as silicone rubber and incorporates a plurality of circular or ring-shaped reinforcement elements 82 joined to the body member. Reinforcement rings 82, optionally slotted rings, are longitudinally spaced from each other along the length of the tubular body member 74 to least inhibit a collapse thereof. Rings 82 may each have a circular cross-section or a rectangular cross-section if formed from a flat strip.

As depicted in FIG. 8, reinforcement rings 82 are embedded in and surrounded by sheath coupling member 74. Alternatively or additionally, sheath coupling member 74 may have helical or ring-shaped reinforcement elements 84 adhered to an inner surface 86 of the coupling member, as shown in FIG. 9, and/or helical or ring-shaped reinforcement elements 88 attached along an outer surface 90 of the coupling member 74, as shown in FIG. 10.

FIG. 11 depicts a sheath coupling or connector 92 in the form of a tubular body member having a first port 94 at a first end and a second port 96 at a second end opposite the first end. Body member 92 has a straight configuration but may be bent or curved, as indicated by arrows 98, upon attachment to a proximal sheath section and a distal sheath section (e.g., 30 and 32 in FIG. 2). Tubular body member 92 is made of a flexible resilient material such as silicone rubber and incorporates at least one helical reinforcement element 100 joined to the body member. Reinforcement element 100 is designed so as to at least inhibit a collapse of sheath coupling body member 92.

Reinforcement element 100 extends circumferentially in multiple turns about the sheath coupling member 92. As discussed above with respect to the embodiments of FIGS. 3-10, reinforcement helix 100 may be embedded in body member 92 or, alteratively, attached along an inner or an outer surface thereof. Also, multiple reinforcement elements may be provided, of similar or different geometries, the multiple reinforcement elements each being embedded in or attached to an inner or an outer surface of the body member.

FIG. 12 depicts a sheath coupling or connector 102 including a tubular body member 104 having at least one expansion-facilitating region 106 for enhancing flexibility of the sheath coupling or connector. Expansion-facilitating region 106 may take the form of a bellows corrugation, e.g., a cross-sectionally semicircular hollow spiraling rib having a smoothly arcuate transverse cross-section bent outwardly from a cylindrical wall of said tubular member, said spiraling outwardly deformed hollow rib having a respective pitch. Tubular body member 104 is connected at one end to a first sheath section 107 and at an opposite end to a second sheath section 108. More particularly, sheath sections 107 and 108 may have annular flanges 110 that insert into tubular body member 104. A layer 112 of adhesive may be provided to fasten tubular body member 104 to each sheath section 107, 108. As described above with reference to other sheath couplings or connectors, sheath coupling or connector 102 defines ports at its opposite ends and a lumen that extends therebetween. Body member 104 has a straight configuration but bendable or curvable, as indicated by arrows 114, upon attachment to sheath sections 107, 108. Tubular body member 104 is made of a flexible resilient material such as silicone rubber or an equivalent composition.

Sheath coupling or connector 102 further includes at least one helical reinforcement element 116 in the form of a coiled strip having a respective pitch and disposed inside tubular body member 104, along an inner surface 118 thereof, longitudinally or axially staggered with respect to spiraling expansion rib 106. The pitch of helical reinforcement element 116 and the pitch of spiraling expansion rib 106 are substantially equal. Helical reinforcement element 116 and expansion rib 106 are wound in opposing directions, and criss-cross at spaced locations along the tubular body member 104. Helical reinforcement element 116 may be attached to inner surface 118 by a layer 120 of adhesive. Adhesive layer 120 may be co-extensive with reinforcement element 116. Alternatively, reinforcement element 116 may be joined to tubular body member 104 only at opposite ends where the reinforcement element is provided with expanded terminal parts 122 and 124 fixed to inner surface 118 by respective adhesive layers 126, 128. In another alternative mode of attachment, helical reinforcement element 116 is force fit into tubular body member 104 and held in place at least in part by frictional forces. In that case tubular bellows member 104 is stretched over spiral reinforcement element 116.

Reinforcement element 116 is made of a thermosetting plastic or polymer material and is designed so as to at least inhibit a collapse of sheath coupling body member 102. Preferably, the interface between reinforcement element 116 and tubular body member 104 is watertight up to 15 psi. The design of FIG. 12 offers the lowest stiffness against similar bending moments.

Although the invention has been described in terms of particular embodiments and applications, one of ordinary skill in the art, in light of this teaching, can generate additional embodiments and modifications without departing from the spirit of or exceeding the scope of the claimed invention. For example, an ultrasonic coupling member or sheath connector as described herein could have reinforcement elements that are longitudinally extending strips or rods that are connected to end caps of a body member and thereby offer resistance to excessive deformation (collapse) of the coupling member or sheath connector. Such linear reinforcement elements may be embedded in or attached to an inner or an outer surface of the tubular body member.

Accordingly, it is to be understood that the drawings and descriptions herein are proffered by way of example to facilitate comprehension of the invention and should not be construed to limit the scope thereof.

What is claimed is:

1. An ultrasonic instrument assembly, comprising:
a handpiece;
a probe or instrument shaft extending from one end of said handpiece;
a proximal sheath portion connected to said handpiece and surrounding a proximal end portion of said probe or instrument shaft;
a distal sheath portion surrounding a distal end portion of said probe or instrument shaft; and
a coupling member including:
a tubular body member having a first port at a first end and a second port at a second end opposite said first end, said body member having a lumen or channel extending from said first end to said second end so that said first and said second port communicate with one another, said body member being made of a flexible resilient material, a proximal end section of said coupling member including said first end being disposed in substantially fluid tight contact with said proximal sheath portion, a distal end section of said coupling member including said second end being disposed in substantially fluid tight contact with said distal sheath portion; and
at least one reinforcement element joined to said body member, said reinforcement element being configured so as to at least inhibit a collapse of said body member, said at least one reinforcement element taking the form of a helical or spiral insert,
said tubular body member being provided with at least one expansion portion in the form of a spiraling outwardly deformed rib, said helical or spiral insert and said rib being longitudinally or axially staggered relative to one another.

2. The ultrasonic instrument assembly set forth in claim 1 wherein said at least one reinforcement element is attached to an inner surface of said body member.

3. The ultrasonic instrument assembly set forth in claim 1 wherein said reinforcement element is made of a more rigid material than the flexible resilient material of said body member.

4. A sheath for an ultrasonic instrument assembly, comprising:
a substantially rigid first sheath section;
a substantially rigid second sheath section;
a tubular body member connected at one end to said first sheath section and at an opposite end to said second sheath section so that said first sheath section and said second sheath section communicate with one another, said body member being made of a flexible resilient material; and
at least one reinforcement element joined to said body member, said reinforcement element configured so as to at least inhibit a collapse of said body member, said at least one reinforcement element taking the form of a helical or spiral insert joined or fixed to said body member only at opposite ends of said helical or spiral insert,
said tubular body member being provided with at least one expansion portion in the form of a spiraling outwardly deformed rib, said helical or spiral insert and said rib being longitudinally or axially staggered relative to one another,
said helical or spiral insert being provided with expanded or enlarged terminal parts that are fixed to said tubular body member.

5. The sheath set forth in claim 4 wherein said reinforcement element is made of a more rigid material than the flexible resilient material of said body member.

6. An ultrasonic instrument assembly, comprising:
a handpiece;
a probe or instrument shaft extending from one end of said handpiece;
a proximal sheath portion connected to said handpiece and surrounding a proximal end portion of said probe or instrument shaft;
a distal sheath portion surrounding a distal end portion of said probe or instrument shaft; and
a coupling member including:
a tubular body member having a first port at a first end and a second port at a second end opposite said first end, said body member having a lumen or channel extending from said first end to said second end so that said first and said second port communicate with one another, said body member being made of a flexible resilient material with a smoothly bendable cylindrical wall, a proximal end section of said coupling member including said first end being disposed in substantially fluid tight contact with said proximal sheath portion, a distal end section of said coupling member including said second end being disposed in substantially fluid tight contact with said distal sheath portion; and
at least one reinforcement element joined to said body member, said reinforcement element being configured so as to at least inhibit a collapse of said body member, said at least one reinforcement element taking the form of a helical or spiral insert disposed on an inner surface of said body member and in said lumen or channel,
said tubular body member being provided with an expansion-facilitating region in the form of a cross-sectionally semicircular spiraling rib that is an outwardly deformed or bent portion of said wall, said helical or spiral insert and said rib being longitudinally or axially staggered relative to one another.

7. The sheath set forth in claim 4 wherein said helical or spiral insert is in the form of a flattened band or strip.

8. The sheath set forth in claim 4 wherein said expansion portion has a cross-section in the form of a circular arc bent outwardly from a cylindrical wall of said tubular member.

9. The ultrasonic instrument assembly set forth in claim 6 wherein said helical or spiral insert is in the form of a flattened band or strip.

10. The ultrasonic instrument assembly set forth in claim 6 wherein said helical or spiral insert is provided with expanded or enlarged terminal parts that are fixed to said tubular body member.

11. The ultrasonic instrument assembly set forth in claim 6 wherein said expansion portion has a smoothly arcuate convex cross-section.

12. The ultrasonic instrument assembly set forth in claim 1 wherein said helical or spiral insert and said rib are wound in opposing directions, so that said helical or spiral insert and said rib criss-cross at spaced locations along the coupling member.

13. The sheath set forth in claim 4 wherein said helical or spiral insert and said rib are wound in opposing directions, so that said helical or spiral insert and said rib criss-cross at spaced locations along the coupling member.

14. The ultrasonic instrument assembly set forth in claim 6 wherein said helical or spiral insert and said rib are wound in opposing directions, so that said helical or spiral insert and said rib criss-cross at spaced locations along the coupling member.

* * * * *